ated under 35

United States Patent
Toth

(10) Patent No.: US 6,716,229 B2
(45) Date of Patent: Apr. 6, 2004

(54) HEMORRHOID RELIEF AND ANAL HYGIENE DEVICE

(76) Inventor: Joseph Toth, 23051 Oak, Dearborn, MI (US) 48128

( * ) Notice: Subject to any disclaimer, the term of this patent is extended or adjusted under 35 U.S.C. 154(b) by 332 days.

(21) Appl. No.: 09/738,093

(22) Filed: Dec. 18, 2000

(65) Prior Publication Data

US 2001/0003157 A1 Jun. 7, 2001

Related U.S. Application Data

(63) Continuation-in-part of application No. 09/258,340, filed on Feb. 25, 1999, now abandoned.

(51) Int. Cl.⁷ .......................... A61M 29/00; A61F 13/20
(52) U.S. Cl. .................................. 606/197; 604/385.01
(58) Field of Search ....................... 606/197; 128/112.1, 128/113.1, 114.1; 604/385.01, 378, 385.17

(56) References Cited

U.S. PATENT DOCUMENTS

| 810,132 A | 1/1906 | Green |
|---|---|---|
| 1,640,416 A | 8/1927 | MacDonald |
| 1,884,089 A | 10/1932 | Millner |
| 1,977,133 A | 10/1934 | Linard |
| 2,057,206 A | 10/1936 | Pohl |
| 2,864,362 A | 12/1958 | Hermanson et al. |
| 5,092,860 A | 3/1992 | Pigneul |
| 5,277,180 A | 1/1994 | Angelillo et al. |
| 5,624,423 A | 4/1997 | Anjur et al. |
| 5,649,917 A | 7/1997 | Roberts et al. |
| 5,672,165 A | 9/1997 | Belecky et al. |
| 5,702,380 A | 12/1997 | Walker |
| 5,820,618 A | 10/1998 | Roberts et al. |
| 5,833,680 A | * 11/1998 | Hartman ............... 604/385.17 |
| 5,873,869 A | 2/1999 | Hammons et al. |
| 5,947,945 A | 9/1999 | Cree et al. |
| 5,993,431 A | 11/1999 | McFall et al. |
| 6,018,093 A | 1/2000 | Roe et al. |

* cited by examiner

*Primary Examiner*—Weilun Lo
*Assistant Examiner*—Linh Truong

(57) ABSTRACT

A hemorrhoid relief and anal hygiene device includes a pressure member for placement between opposing buttock surfaces in the natal cleft adjacent to the anus of the user. The pressure member has opposite side faces for each positioning against one of the opposing buttock surfaces of the user. The pressure member has a perimeter wall extending between the opposite side faces with first, second, and third sections. The first and second sections have inboard ends converging at a protruding crest for partial insertion in the anus. The first and second sections are concave for abutting opposite areas of the surface of the anus. The third section extends between outboard ends of the first and second sections. A second embodiment of the device includes a bulbous central portion having a substantially spherical shape and a pair of elongate side members extending outwardly from opposite sides of the central portion. Each side member has a substantially circular cross section with a diameter that increases from the free end toward the base end.

13 Claims, 2 Drawing Sheets

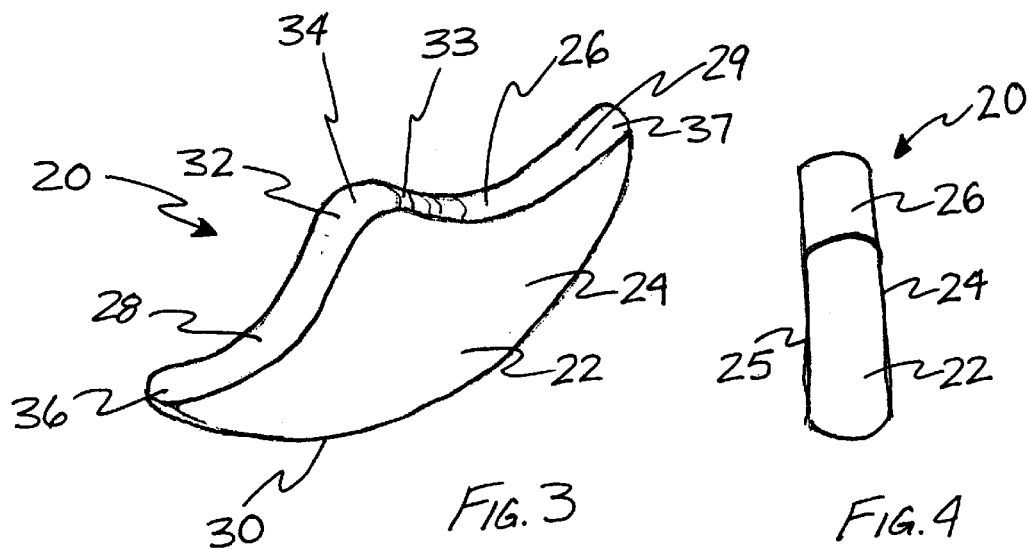
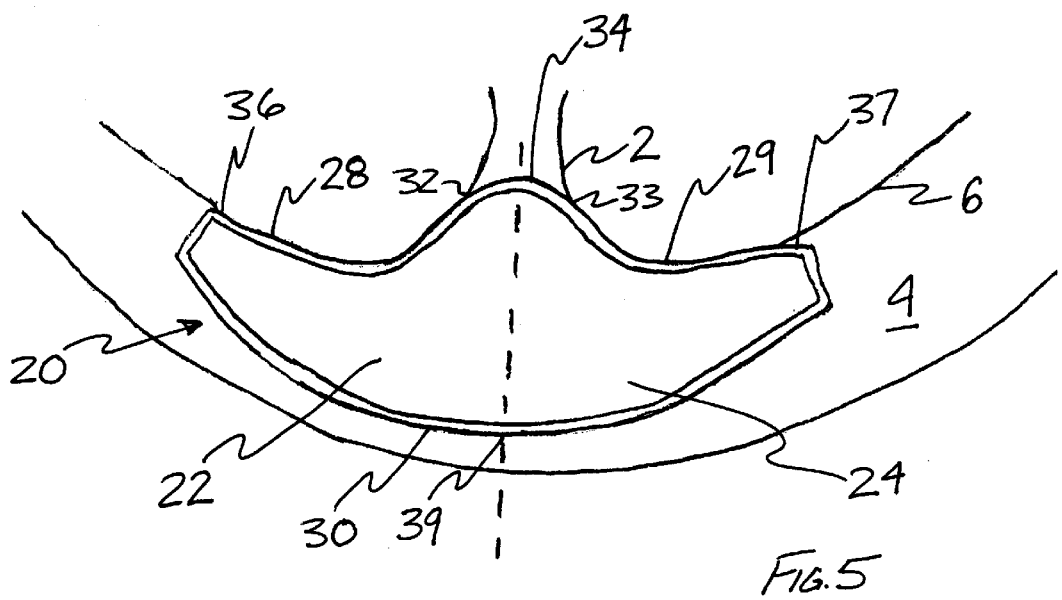

HEMORRHOID RELIEF AND ANAL HYGIENE DEVICE

REFERENCE TO RELATED APPLICATION

This application is a continuation-in-part patent application of patent application Ser. No. 09/258,340, filed Feb. 25, 1999 now abandoned.

BACKGROUND OF THE INVENTION

1. Field of the Invention

The present invention relates to hemorrhoid relief devices and more particularly pertains to a new hemorrhoid relief and anal hygiene device for providing a user with hemorrhoid relief and promoting anal hygiene.

2. Description of the Prior Art

The use of hemorrhoid relief devices is known in the prior art. Devices have been proposed which employ belts and straps, but these devices can be uncomfortable and may be unsanitary if not disposable. Other devices have been proposed that, while avoiding the use of belts and straps, are highly invasive for the purpose of applying pressure to the affected area, which requires insertion through an often painfully-inflamed anus. These known devices and apparatuses have thus been less than desirable for those desiring a sanitary and minimally invasive solution to the problem of hemorrhoids.

In these respects, the hemorrhoid relief and anal hygiene device according to the present invention substantially departs from the conventional concepts and designs of the prior art, and in so doing provides an apparatus primarily developed for the purpose of providing a user with hemorrhoid relief and promoting anal hygiene.

SUMMARY OF THE INVENTION

In view of the foregoing disadvantages inherent in the known types of hemorrhoid relief devices now present in the prior art, the present invention provides a new hemorrhoid relief and anal hygiene device construction wherein the same can be utilized for providing a user with hemorrhoid relief and promoting anal hygiene.

The general purpose of the present invention, which will be described subsequently in greater detail, is to provide a new hemorrhoid relief and anal hygiene device apparatus and method which has many of the advantages of the hemorrhoid relief devices mentioned heretofore and many novel features that result in a new hemorrhoid relief and anal hygiene device which is not anticipated, rendered obvious, suggested, or even implied by any of the prior art hemorrhoid relief devices, either alone or in any combination thereof.

To attain this, the present invention generally comprises a pressure member for placement between opposing buttock surfaces in the natal cleft adjacent to the anus of the user. The pressure member has opposite side faces for each positioning against one of the opposing buttock surfaces of the user. Each of the side faces of the pressure member is substantially planar. Each of the side faces of the pressure member lie in substantially parallel planes. The pressure member has a perimeter wall that extends between the opposite side faces. The perimeter wall has a first section, a second section, and a third section. The first and second sections of the perimeter wall has inboard ends converging at a protruding crest adapted for partial insertion in the anus of the user. The first and second sections are concave for abutting opposite areas of the surface of the anus. The third section extends between outboard ends of the first and second sections. In a second embodiment of the invention, the device includes a bulbous central portion having a substantially spherical shape. A pair of elongate side members is coupled to and extends outwardly from opposed sides of the central portion. Each of the elongate side members has a length between a base end mounted on the central portion and a free end. Each of the elongate side members has a substantially circular cross section. A diameter of the each of the elongate side members increases from the free end toward the base end. A longitudinal axis of each of the side members is arcuate such that the side members form an arc with an inward surface having a portion of the central portion protruding from the inward surface.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new hemorrhoid relief and anal hygiene device apparatus and method which has many of the advantages of the hemorrhoid relief devices mentioned heretofore and many novel features that result in a new hemorrhoid relief and anal hygiene device which is not anticipated, rendered obvious, suggested, or even implied by any of the prior art hemorrhoid relief devices, either alone or in any combination thereof.

It is another object of the present invention to provide a new hemorrhoid relief and anal hygiene device that may be easily and efficiently manufactured and marketed.

It is a further object of the present invention to provide a new hemorrhoid relief and anal hygiene device that is of a durable and reliable construction.

An even further object of the present invention is to provide a new hemorrhoid relief and anal hygiene device which is susceptible of a low cost of manufacture with regard to both materials and labor, and which accordingly is then susceptible of low prices of sale to the consuming public, thereby making such hemorrhoid relief and anal hygiene device economically available to the buying public.

Still yet another object of the present invention is to provide a new hemorrhoid relief and anal hygiene device which provides in the apparatuses and methods of the prior art some of the advantages thereof, while simultaneously overcoming some of the disadvantages normally associated therewith.

Still another object of the present invention is to provide a new hemorrhoid relief and anal hygiene device for providing a user with hemorrhoid relief and promoting anal hygiene.

Even still another object of the present invention is to provide a pressure member for placement between opposing buttock surfaces in the natal cleft adjacent to the anus of the user. The pressure member has opposite side faces for each positioning against one of the opposing buttock surfaces of the user. Each of the side faces of the pressure member is substantially planar. Each of the side faces of the pressure member lie in substantially parallel planes. The pressure member has a perimeter wall that extends between the opposite side faces. The perimeter wall has a first section, a second section, and a third section. The first and second sections of the perimeter wall has inboard ends converging at a protruding crest adapted for partial insertion in the anus of the user. The first and second sections are concave for abutting opposite areas of the surface of the anus. The third section extends between outboard ends of the first and second sections.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic perspective view of an optional embodiment of the hemorrhoid relieving device of the invention.

FIG. 4 is a schematic end view of the optional embodiment of the invention.

FIG. 5 is a schematic side view of the optional embodiment in position adjacent buttock surfaces in the natal cleft adjacent to the anus of the user.

DESCRIPTION OF THE PREFERRED EMBODIMENT

With reference now to the drawings, and in particular to FIGS. 1 through 5 thereof, a new hemorrhoid relief and anal hygiene device embodying the principles and concepts of the present invention will be described.

Figure 1:
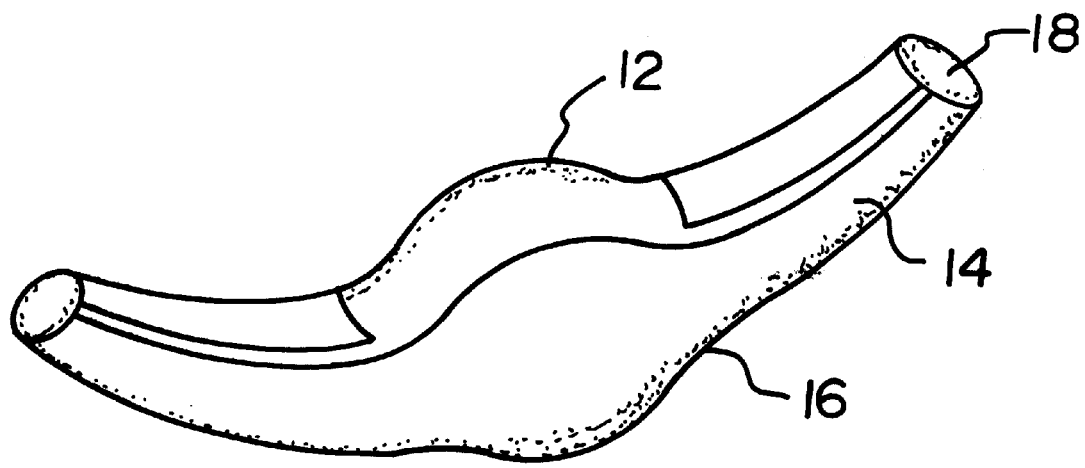
FIG. 1 is a schematic perspective view of a new hemorrhoid relief and anal hygiene device according to the present invention.
Figure 2:
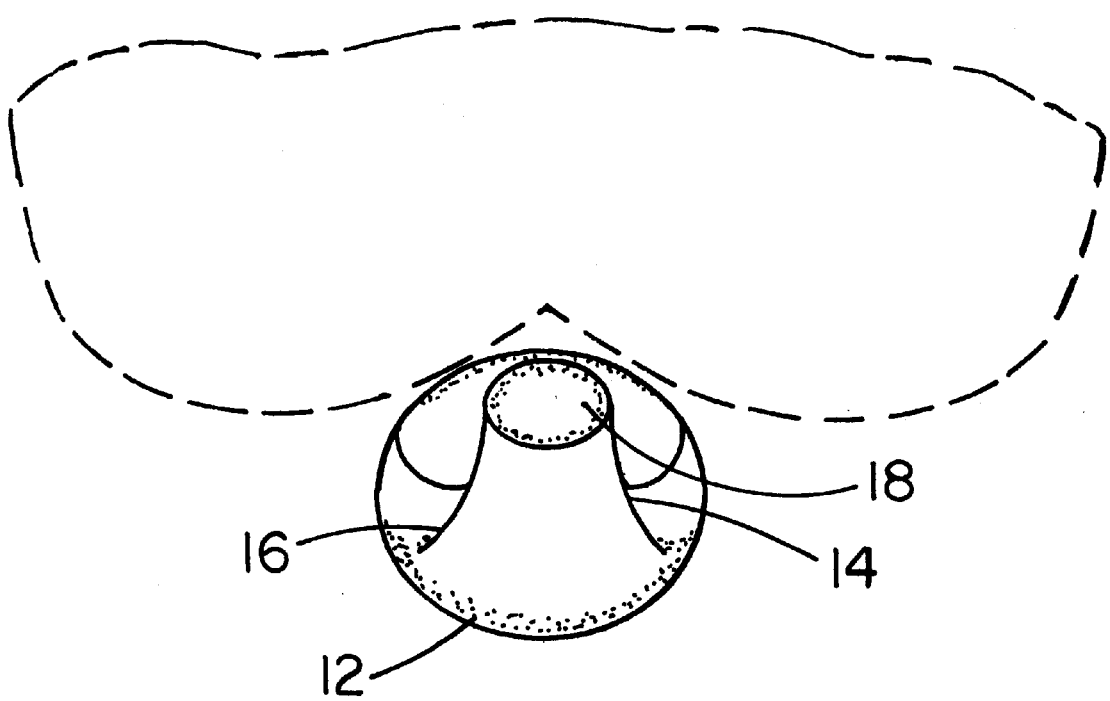
FIG. 2 is a schematic front view of the present invention during use.

A first embodiment of the present invention, designated as numeral 10 and shown in FIGS. 1 and 2, includes a solid central portion 12 constructed entirely of an absorbent, flexible, resilient cotton or paper material or any other type of material employed in the tampon arts. The central portion has a substantially spherical configuration.

As shown in FIG. 1, also included is a pair of side members 14 each constructed entirely of an absorbent, flexible, resilient cotton or paper material similar to that from which the central portion is constructed. The side members are each equipped with a generally cylindrical configuration. Inboard ends 16 of the side members are integrally formed on diametrically opposed points on the central portion. The side members each thus extend from the central portion for terminating in a free outboard end 18 with a planar circular configuration.

With continuing reference to FIG. 1, each side member has an inboard diameter about ½ that of the central portion. Associated therewith is an outboard diameter of about ½ that of the inboard diameter. As such, a diameter of the side member continuously tapers from the inboard end to the outboard end thereof. Further, a length of each side member is about twice the diameter of the solid central portion while maintaining a circular cross-section along the entire length thereof. For conforming to a buttocks of a user, a longitudinal axis of each side member defines a radius of curvature greater than that of an outer surface of the central portion. By this structure, the outboard ends of the side members extend upwardly.

FIG. 1 shows adhesive strips each with a generally rectangular configuration positioned on an upper convex surface of one of the side members. Ideally a length of each adhesive strip is similar to that of the associated side member. Further, a width of each adhesive strip is about ½ a circumference of the side member. As such, the width of each adhesive strip tapers as the circumference and diameter of the associated side member decreases from the inboard end to the outboard end thereof. Associated with the adhesive strips is a pair of waxed paper strips each having a size and shape similar to those of the adhesive strips. In use, the waxed paper strips are adapted for being removably coupled over the adhesive such that the side members may be selectively adhered to a buttocks of a user.

Impregnated within the central portion is a hemorrhoid medical ointment or solution for application on an anus of a user during use. As an option, a lubricating agent may further be applied to the central portion and side members. It should be noted that also impregnated within the central portion is an odor inhibitor in the form of a scent, charcoal, or the like for concealing odors. In use, the central portion is adapted to be positioned within a buttocks of user such that the side members remain on opposite sides of an anus of the user, as shown in FIG. 2. As such, a user is provided with hemorrhoid relief and any anal discharge resulting from mild anal incontinence may be absorbed.

An optional and highly preferred embodiment of the invention provides a hemorrhoid relieving device 20 (see FIGS. 3 through 5) for applying pressure to swollen tissues of the anus 2 of the user, while being minimally invasive and highly comfortable.

The hemorrhoid relieving device 20 includes a pressure member 22 for placement between opposing buttock surfaces 4 in the natal cleft 6 adjacent to the anus 2 of the user. The pressure member 22 has opposite side faces 24, 25 for each positioning against one of the opposing buttock surfaces of the user. Each of the side faces of the pressure member are preferably substantially planar for forming a relatively large surface for aiding in holding the pressure member in place between the buttock surfaces, and especially facilitating clenching of the opposing buttock surfaces on the pressure member. Preferably, each of the side faces of the pressure member lie in substantially parallel planes for maximizing the surface against which the opposing buttock surfaces abut against.

The pressure member 22 has a perimeter wall 26 that extends between the opposite side faces 24, 25. The perimeter wall has a first section 28, a second section 29, and a third section 30. The first 28 and second 29 sections of the perimeter wall have inboard ends 32, 33 that converge at a protruding crest 34 adapted for partial insertion in the anus of the user. The first 28 and second 29 sections are concave for abutting opposite areas of the surface of the anus. The third section 30 extends between outboard ends 36, 37 of the first 28 and second 29 sections. The third section 30 of the perimeter wall may be convex. The perimeter wall 26 of the pressure member may bulge outward between the side faces 24, 25. An axis 36 of symmetry may extend through the crest 34 and a midpoint 38 of the third section 30 of the perimeter wall so that the pressure member may be positioned with either of the first and second sections of the perimeter wall forward and be equally effective.

Most preferably, the pressure member 22 may be formed of an absorbent material, such as, for example, a fibrous material including paper or cotton. Optionally, the pressure member 22 may be impregnated with various substances as described above. As a further option, a light-strength adhesive may be applied to the side faces of the pressure member to help facilitate the retention of the member between the buttocks.

In one illustrative embodiment of the invention, the pressure member has a length between the outboard ends of the first and second sections of the perimeter wall of approximately 9 centimeters, and a width between the crest and the midpoint of the third section of approximately 4 centimeters. The thickness of the pressure members between the side faces is approximately 1 centimeter.

The pressure member is thus positionable and easily held between the opposing buttock surfaces by the user, while applying pressure to the surface of the anus that imparts a gentle retaining pressure directly to the distressed tissue, and can restrict the growth and inflammation of any skin tags or protrusions on the anus.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A hemorrhoid relief and anal hygiene device for placing adjacent to an anus of a user, the device comprising:

a bulbous central portion having a substantially spherical shape;

a pair of elongate side members coupled to and extending outwardly from opposed sides of the central portion, each of the elongate side members having a length between a base end mounted on the central portion and a free end, each of the elongate side members having a substantially circular cross section, a diameter of the each of the elongate side members increasing from the free end toward the base end, a longitudinal axis of each of the side members being arcuate such that the side members form an arc with an inward surface having a portion of the central portion protruding from the inward surface;

wherein the central portion is adapted to be positioned adjacent to a buttocks of a user such that the side members are adjacent an anus of the user;

wherein the central portion and the side members have a circular cross-section along an entire length of the central portion and side members.

2. A device as set forth in claim 1 wherein the central portion and side members are each, constructed entirely of an absorbent, flexible, resilient material.

3. A device as set forth in claim 1 wherein the material is paper.

4. A device as set forth in claim 1 wherein the material is cotton.

5. A device as set forth in claim 1 wherein the side members each have an inboard diameter less than that of the central portion such that the central portion protrudes from the side members.

6. A device as set forth in claim 5 wherein the side members each have a substantially planar surface at the free end of the side member.

7. A device as set forth in claim 1 further including adhesive positioned on the side member.

8. A device as set forth in claim 1 further including medical ointment applied to the central portion for application on the anus of the user.

9. A device as set forth in claim 1 further including an odor inhibitor applied to the central portion for concealing odors.

10. A device as set forth in claim 6 wherein the substantially planar surface at the free end of the side members is substantially circular.

11. A hemorrhoid relief and anal hygiene device for placing adjacent to an anus of a user, the device comprising:

a bulbous central portion having a substantially spherical shape;

a pair of elongate side members coupled to and extending outwardly from opposed sides of the central portion, each of the elongate side members having a length between a base end mounted on the central portion and a free end, each of the elongate side members having a substantially circular cross section, a diameter of the each of the elongate side members increasing from the free end toward the base end, a longitudinal axis of each of the side members being arcuate such that the side members form an arc with an inward surface having a portion of the central portion protruding from the inward surface;

wherein the central portion is adapted to be positioned adjacent to a buttocks of a user such that the side members are adjacent an anus of the user;

wherein the central portion and side members are each constructed entirely of an absorbent, flexible, resilient material;

wherein the central portion and the side members have a circular cross-section along an entire length of the central portion and side members;

wherein the side members each have an inboard diameter less than that of the central portion such that the central portion protrudes from the side members;

wherein the side members each have a substantially planar surface at the free end of the side member;

wherein the substantially planar surface at the free end of each of the side members is substantially circular;

adhesive being positioned on the side members;

medical ointment being applied to the central portion for application on the anus of the user; and an odor inhibitor applied to the central portion for concealing odors.

12. A device as set forth in claim 11 wherein the material is paper.

13. A device as set forth in claim 11 wherein the material is cotton.

* * * * *